United States Patent [19]

Foser

[11] Patent Number: 5,782,632
[45] Date of Patent: Jul. 21, 1998

[54] SUPPORT PLATE FOR TEETH

[75] Inventor: Hans-Peter Foser, Balzers, Liechtenstein

[73] Assignee: Ivoclar AG, Liechtenstein

[21] Appl. No.: 612,805

[22] Filed: Mar. 11, 1996

[30] Foreign Application Priority Data

Mar. 10, 1995 [DE] Germany ............ 195 08 760.7

[51] Int. Cl.$^6$ ............ A61C 13/12; A61C 19/10
[52] U.S. Cl. ............ 433/26; 206/83
[58] Field of Search ............ 433/26, 34, 77; 206/63.5, 83; D24/181

[56] References Cited

U.S. PATENT DOCUMENTS

| | | | |
|---|---|---|---|
| 74,971 | 3/1868 | Asays | 206/83 |
| D. 150,509 | 8/1948 | Myerson | D24/181 |
| 1,634,687 | 7/1927 | Sanders | 206/83 |
| 1,938,222 | 12/1933 | Green | 206/83 |
| 2,193,988 | 3/1940 | Sheppard | 206/83 |
| 2,243,583 | 5/1941 | Stein | |
| 2,269,780 | 1/1942 | Myerson | 206/83 |
| 2,363,997 | 11/1944 | Rothman | 206/83 |
| 2,874,487 | 2/1959 | Bloom et al. | 206/83 |
| 3,111,760 | 11/1963 | Semmelman et al. | 433/26 |
| 4,306,860 | 12/1981 | Janssen et al. | 433/26 |

FOREIGN PATENT DOCUMENTS

| | | | |
|---|---|---|---|
| 1011717 | 7/1957 | Germany | 433/26 |
| 7403850 | 2/1974 | Germany. | |
| 2947094 | 5/1981 | Germany. | |
| 3831919 A1 | 4/1989 | Germany. | |
| 92 14 839.5 | 2/1993 | Germany. | |
| 662026 | 11/1951 | United Kingdom | 206/83 |

*Primary Examiner*—Nicholas D. Lucchesi
*Assistant Examiner*—Ralph A. Lewis
*Attorney, Agent, or Firm*—John C. Thompson; Alan S. Korman

[57] ABSTRACT

A support plate assembly (10) for teeth which includes a plate-like body (12) with external dimensions that may be strung together, and a substantially flat, quadrilateral wax receiving portion (22) for the acceptance of an adhesive wax or the equivalent into which a plurality of teeth may be pressed, one next to the other. The wax receiving portion (22) is delimited by convex, forward-thrusting arched upper and lower ridges (14, 16), and lateral ridges. A flat strip of wax is held in the wax receiving portion such that the wax receiving portion has a greater depth at the center area intended for premolar than at the lateral areas intended for molars.

7 Claims, 1 Drawing Sheet

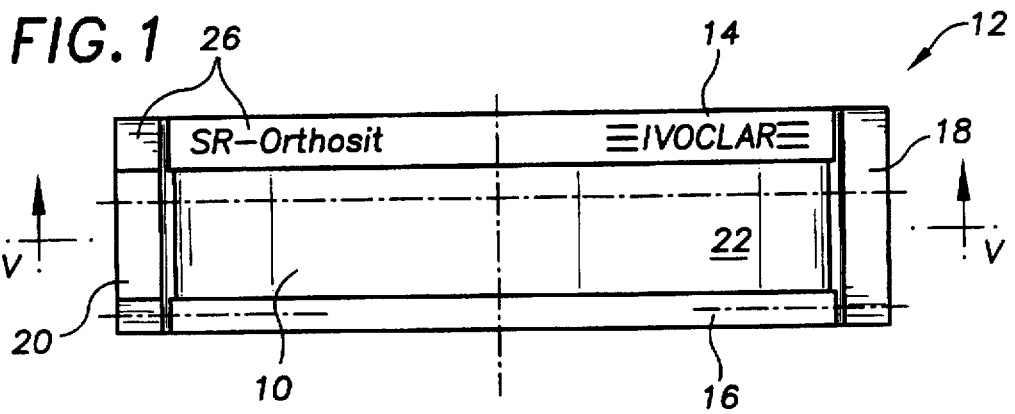
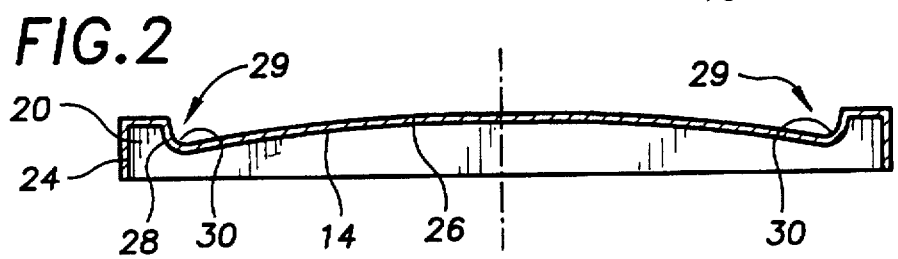
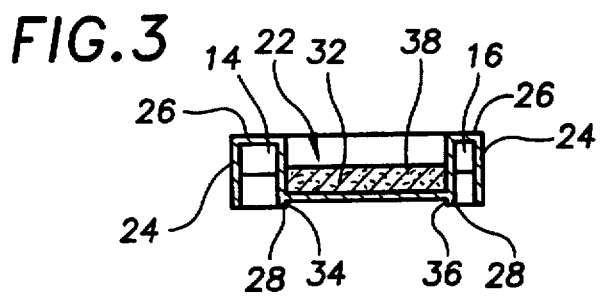
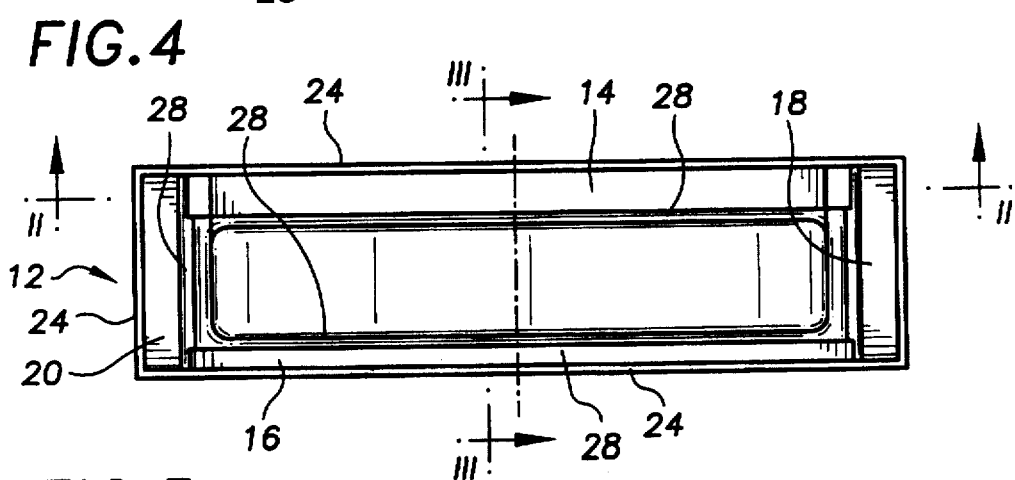
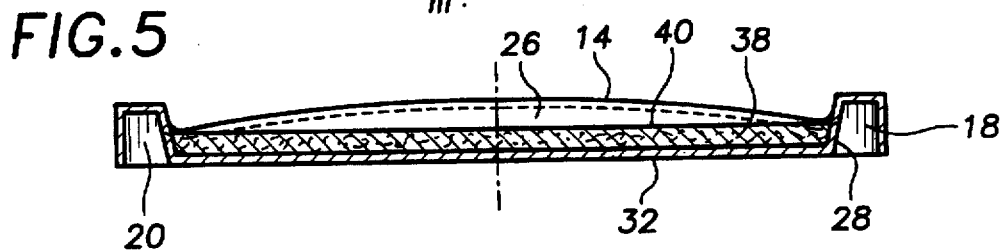

SUPPORT PLATE FOR TEETH

TECHNICAL FIELD

The invention relates to a support plate for teeth used in making dentures, and more specifically to a novel support plate for teeth having a quadrilateral wax receiving body having a quadrilateral wax receiving portion, the boundaries of which are marked off by upper and lower ridges and two lateral ridges.

BACKGROUND OF THE INVENTION

Support plates for teeth have been known for a long time. They include a substantially quadrilateral plate-like body having a wax receiving portion, which extends obliquely in the form of a groove, also substantially quadrilateral in form, flatly across the plate-like body. Upper and lower ridges are provided above and below the groove, which ridges protrude accordingly, and may be used for the purpose of written labels. In addition, these surfaces afford protection for the teeth that are to be applied to the groove, and, in their breadth, they render adaptation to various types of teeth, such as front teeth and molars, possible.

The wax receiving portion is filled with adhesive wax or the equivalent for the purpose of securely positioning the teeth. Thus, instead of adhesive wax, other substances, such as plastics that have a certain adhesive capacity, may be used as well, but adhesive wax is most commonly used. In point of fact, in the long term, adhesive wax has an enhanced viscosity, that is to say it is nearly solid at room temperature, and therefore, it lends itself particularly well to the desired positioning of the teeth. This type of wax is also referred to as "carding wax" in the trade.

The teeth are pressed into this wax in the desired manner, as a result of which, a certain depression in the wax mass comes into being. It is desirable that if necessary, the teeth may be removed, but re-set in their former positions, without the unintentional loosening of individual teeth from their positions in the waxen mass.

Positioning in a waxen mass has basically proven its value over decades and is, in particular, better-suited than positioning in individual, molded recesses over adhesive substances, as was suggested, for example, in the German utility patent DE-GM 74 03 850 and the German published application DE-OS 29 47 094.

Indeed, such positioning, in conjunction with the corresponding adjustment of the individual recesses to the basal surfaces of the teeth, affords support that is quite good. According to the above German patent application, the support may assume the form of an arc, much like the natural curvature of the jaw, for example. In the case of this embodiment, however, support in the middle area is virtually absent, so that the support plate can be bent quite readily if a tooth is pressed back into place in the middle. In this way, the danger exists that the teeth that are located next to the tooth that was pressed back into place may be loosened, or even pressed out from their individual recesses, which are also deformed at that time.

Furthermore, in the case of the solution according to DE-OS 29 47 094, it is disadvantageous that the individual recesses must be adapted to the various forms of teeth. This necessitates keeping a considerable number of different support plates for teeth in supply if a sufficient degree of support for the teeth is desired. If, in point of fact, nothing more than an imprecise adjustment to the form of the tooth is undertaken, the danger is present that the tooth in question does not make proper contact with the adhesive that is provided in a small trough, or, that it is guided so poorly laterally, that certain acceptance is not assured. For this reason, this support plate for teeth has not prevailed.

An additional problem of well-known support plates for teeth is supporting the teeth in the transverse direction. Just for the purpose of keeping the quantity of the requisite wax low, the wax-receiving area is rendered as narrow as possible. On the other hand, the support plate for teeth must lend itself to the accommodation of teeth of varying sizes, such as, for example, both molars and front teeth. In this process, the front teeth are pressed into the wax in a lying position, such that, for example, the appropriate canines will follow a medially applied row of front teeth, one on the right and one on the left. A canine is regularly somewhat larger and stronger than the front teeth.

If lateral teeth are presented on the support plate for teeth, it holds, accordingly, that the laterally applied molars are regularly larger and stronger than the medially-positioned pre-molars. In practice, it is shown that the sturdier teeth are also inserted more forcefully. Then, however, removal by perpendicular pulling is practically impossible; rather, to effect removal, the tooth must be tilted. This has its grounds in the fact that the adhesive wax must have a sufficient adhesive reserve to adhere at temperatures that are rather high, as well as at temperatures that are rather low, so that the adhesive strength at normal room temperature is quite high.

OBJECTS AND SUMMARY OF THE INVENTION

By contrast with these considerations, it is the underlying task of the invention to create a support plate for teeth which permits better usage, given the various sizes and shapes of the teeth, in the case of which, the utilization of a comparably slight quantity of wax is rendered possible.

According to the invention, this task is met by providing a support plate assembly for teeth having a plate body provided with a substantially flat quadrilateral wax receiving unit for the receival of a highly viscous mass, such as wax, into which a plurality of teeth may be positioned, one next to the other, which wax receiving unit is demarcated by an upper and a lower ridge and two lateral ridges that protrude from the bottom of the wax receiving unit, in which the upper ridge and the lower ridge are vaulted or arched toward the front so as to protrude from the bottom. It is understood that in this instance, a wax receiving unit, or portion, is taken to mean a substantially flat, quadrilateral receiving surface for an adhesive mass, which fills up, across its entire surface, the area between the upper, lower, and lateral ridges. The adhesive mass may be any adhesive wax, but it is not restricted to wax in the chemical sense. A flat strip of wax may be inserted into the quadrilateral portion so that it lies on the bottom, or it may be poured in, and it is held in the wax receiving portion in such a manner that it cannot be lost.

Each of the upper and lower ridges have arched upper surfaces, and therefore it is possible, surprisingly, to achieve several advantages. The medially-arranged pre-molars are better protected with respect to unintentional lateral pressure that could result in loosening and release by the upper and lower ridges, which extend upward like an apron. By contrast, the molars, which are arranged at the end of the support plate for teeth, afford a better lateral surface of attack, due to the fact that the upper and lower ridges at this point are practically drawn downward. Accordingly, these teeth may be more readily released by tilting.

When a front/canine denture set is used in the support plate for teeth according to the invention, there is the additional advantage that the canines that are applied at the ends may be set more deeply, inasmuch as they do not so readily make contact with the upper and lower ridges. Due to the flat positioning of front/canine teeth, they regularly protrude into the areas of the upper and lower ridges beyond the surface of the adhesive wax. With this embodiment, accordingly, the median front teeth are prevented from springing back with respect to the canines. Depending upon the degree of vaulting or arching from the front, it is also possible to cause the median front teeth to advance with respect to the canines, which affords an aesthetically more favorable impression in the presentation of the teeth on the dental plate.

When using the support plate for teeth according to the invention for front teeth/canines, there is the additional advantage that in the case of the usual impression process, in which smaller teeth are not pressed as deeply as larger teeth—all teeth can be supported uniformly on the edges of the upper and lower ridges, thus assuring a sort of three-point anchoring, which is very stable, or at least, such that a positioning on one edge, thus, either on the edge of the upper ridge that is adjacent to the wax receiving portion, or upon that of the lower ridge. Removal is then rendered relatively easily possible by gripping the point, whereby, in addition—in keeping with the use of molars and pre-molars—there is a somewhat enlarged gripping area in the case of the canines which are applied at the ends.

As a result of the flat embodiment of the bottom, on the other hand, good application and support of the acceptance body of wax is possible, so that the support plate for teeth is not deformed when the teeth are pressed into place, even if a relatively slight thickness of material is used for the body of the plate.

The lateral ridges are elevated above the adjacent areas of upper and lower ridges. They then provide a sort of protection against impact, so that the teeth are protected, not only by the moderately highly arched upper and lower ridges, but also by the lateral ridges on all sides. In spite of the lateral ridges, which are upwardly extended, in the case of this embodiment of the invention, the accessibility of the molars is assured without further ado by virtue of the fact that in the lateral grasping areas of the molars, the upper and lower ridges are practically reduced.

In one advantageous embodiment, provision is made for a supporting flange of minimal height to surround the bottom of the wax receiving portion, with respect to the underlying support. By these means, it is possible to avoid the application to a specific area, which is, in many instances, not desired, and if the bottom should, indeed, be perforated as a result of pressure by the slight height of the support flange, this does no harm, due to the fact that the adhesive wax has a certain degree of elasticity, so that the adjacent teeth are not loosened by the application of pressure.

Preferably, the ridges are embodied so as to be hollow, which provides benefits in terms of savings in material and the weight of the support plate for teeth.

As a result of the protrusive arching of the upper and lower ridges, in addition, the teeth are presented in an aesthetically pleasing manner, for by these means, the natural orientation of the teeth is intimated without adversely affecting, for example, the ability to stack and store the support plates for teeth. In this regard, it is also favorable if the more robust and thicker teeth that are arranged at the ends are somewhat recessed, due to the fact that by these means the overall height of the support plate for teeth, with the teeth set in place, is diminished somewhat, which can be significant if a large number of various types of teeth is to be stored within the context of an assortment of teeth.

In addition, the embodiment, which is comprised of the protruding, arched upper and lower ridges, affords an improved lateral view and it is possible, prior to the removal of the teeth, for the prosthesis to be introduced, to assess the optical impression of the teeth in the lateral view as well.

Furthermore, it is particularly favorable if the support plate for teeth according to the invention is produced from a dark material, and if, for example, a darkened wax that has been colored with carbon black, for instance, is used. Due to the close proximity to the forward arched upper and lower ridges, the translucence of the teeth is shown to better effect and the tooth assumes a more gleaming appearance.

Additional advantages, details, and characteristics result from the following description of an embodiment example in conjunction with the drawing.

BRIEF DESCRIPTION OF THE DRAWINGS

FIG. 1 shows a view from the top onto a form of embodiment of a support plate for teeth according to the invention;

FIG. 2 shows a section through the support plate for teeth according to FIG. 1 along the line II—II from FIG. 4;

FIG. 3 shows a section of the support plate for teeth in the embodiment form according to FIG. 1, along the line III—III from FIG. 4;

FIG. 4 shows a view of the support plate for teeth according to FIG. 1 from the bottom, and FIG. 5 shows a section along the line V—V according to FIG. 1.

DETAILED DESCRIPTION

The support plate assembly 10 for teeth shown in FIG. 1 includes a plate body 12, which is designed for the acceptance of wax 38 shown in FIGS. 3 and 5, into which teeth, not shown, may be introduced. The body of the plate 12 includes an upper ridge 14 and a lower ridge 16, as well as two lateral ridges, 18 and 20. A wax receiving portion 22 extends in the area between these ridges 14 through 20. The wax receiving portion 22 includes a substantially flat, quadrilateral receiving surface or bottom 32 onto which an adhesive mass is placed, which fills up, across the entire bottom the area between the ridges 14 through 20.

In the case of the example, the upper ridge 14 is somewhat broader than the lower ridge 16. It is understood that the dimensions may be selected to meet the need, and they can, for example, be such as to give due consideration to any labelling that is desired, as FIG. 1 shows such labeling on the upper ridge.

All ridges include, as FIG. 3 shows more readily, outer legs 24, middle legs 26, and inner legs 28, and they have, accordingly, a substantially U-shaped fundamental structure, and they are hollow. This embodiment benefits the stability of the body of the plate 12.

As FIG. 2 more readily shows, upper ridge 14 exhibits a convex, forward-thrusting arched fundamental structure with a correspondingly forward-thrusting arched middle leg 26. The protruding arching occurs to such a distance that the height of the upper ridge 14 is, in the middle, approximately of equal height to the elevation of the lateral legs, 18 and 20.

As seen in FIG. 1, the lateral areas 29 of the upper ridge 14 have a lower height than the adjacent lateral ridge. While not fully shown, the lower ridge also has the same shape as the upper ridge except that the surface 26 is narrower. Thus, it has an intermediate portion of the same height as the lateral ridges 18 and 20, and lower lateral portions similar to the portions 29 of the upper ridge 14. In the case of the transition to the lateral ridge from each of the upper and lower ridges, a radius 30 is provided, which connects the middle leg 26 of the upper and lower ridges ridge 14 and 16 with the inner leg 28 of the lateral ridges 18 and 20. This inner radius 30 may be provided on an order of magnitude ranging from 0.5 to 5 mm, in particular from about 1.5 to 2 mm, and it renders the gentle connection of one ridge to the other. The inner leg 28 of the lateral ridges 18 and 20, follows a course that is somewhat oblique, and it approximates, in continuation of the radius of the forward-thrusting arching of the upper ridge 14. As FIG. 5 more readily shows, the inner leg 28 of the lateral ridge 18 or 20 respectively, continues to the bottom 32 of the wax receiving portion 22 in the same way.

From FIG. 3, in conjunction with FIGS. 1 and 2, the overall box-like structure of the body of the plate according to the invention may be seen. Despite the arching, which is visible from FIGS. 2 and 5, the external dimensions of the plate body 12, (apart from those areas 29 on the side, next to the lateral ridges 18 and 20, which serve as notches,) are substantially flat and quadrilateral in shape, which is decidedly advantageous from the standpoint of maneuverability, and the ability to add on to the construct. The length of the support plate for teeth may, for example, be 59 mm±4 mm for a denture for six teeth, especially front teeth, or 86 mm±4 mm for a denture for eight teeth, especially for molars and pre-molars. The width, that is the transverse extent across upper and lower ridges 14, 16 is, in both cases, 22 mm±3 mm. With these dimensions, it is possible to realize a modular concept that is capable of being added to. The radius of the upper and lower ridge 14 and 16 may range between 50 and 500 mm, preferably between 50 and 300 mm, and particularly, between 80 and 120 mm for narrower support plates 12 for teeth, and between 220 and 260 mm for wider support plates for teeth.

As FIG. 3 shows furthermore, the bottom 32 of the wax receiving portion 22 is supported by support flanges 34 and 36, which are quite short, laterally adjacent to the ridges 14 and 16. In the space between the support flanges 34 and 36 on the bottom 32, it is possible, for example, for discreet writing to be applied.

Even the outer legs 24 of the ridges 14 and 16 are each drawn downward quite far and serve to furnish support upon an underlying surface that is not shown here.

From FIG. 4 it is possible to see that the support plate 12 for teeth is open from the rear, and it covers a hollow space in a form that lies upon an underlying surface. The use of profiled hollow material serves to provide stability in addition to relative savings in terms of weight, and it is thus cost-effective from the standpoint of production costs at the same time. Here, as in the other figures as well, the same parts are identified with the same reference symbols.

It is possible to see that in the case of such an embodiment example, the wax receiving portion 22 takes up considerably more than half the total surface area of the support plate 12 for teeth. It is understood that this portion may be broadly adapted to the particular requirements, and, in particular, that it may constitute somewhat less than half.

As FIG. 5 shows, the ridges 14 and 16, of which, the upper ridge 14 from FIG. 5 may be seen, exhibit a curvature, whereas the bottom 32 is flat. The distance between the bottom 32 and the middle leg 26 of the ridges 14 and accordingly increases and then decreases again across the longitudinal expanse of the wax receiving portion 22 in the case of this embodiment. A flat strip of wax 38 may be inserted onto the quadrilateral surface, or it may be poured in, and it is held in the wax receiving portion 22 in such a manner that it cannot be lost. It can be seen that the upper surface 40 of the adhesive wax is flat, and this permits centrally located teeth to be protected by the central arched portion of the upper and lower ridges 14 and 16.

If necessary, an undercut may also be provided in the inner leg 28, the lateral ridge 18 and 20 in each case. If necessary, this renders the anchoring of the wax strip in the wax receiving portion 22 possible. In the following claims adhesive wax should be construed to include its equivalents as set forth above.

What is claimed is:

1. A support plate assembly for teeth comprising:

a plate body (12) having a substantially flat quadrilateral wax receiving portion (22) having a bottom 32 for the reception of an adhesive wax in which a plurality of teeth may be positioned, one next to the other, upper, lower, and two spaced apart lateral ridges (14, 16, 18, and 20, the two spaced apart lateral ridges each having spaced apart portions adjacent the upper and lower ridges, which upper, lower and two lateral ridges mark off the boundaries of the wax receiving portion, and which ridges protrude from the bottom (32) of the wax receiving portion (22), the upper ridge (14) and the lower ridge (16) being arched away from the bottom so that the central portion of each ridge protrudes from the bottom (32) a greater extent than their lateral areas (29); and a flat strip of wax held in the wax receiving portion such that the wax receiving portion has a greater depth at the center area intended for premolars than at the side area intended for molars.

2. The support plate assembly for teeth according to claim 1 characterized in that the lateral ridges (18, 20) extend away from the bottom a further amount than adjacent portions of the upper (14) and lower (16) ridges.

3. The support plate assembly for teeth according to claim 1, wherein at least one of the arched protruding upper (14) or lower (16) ridges exhibits a central height that approximately corresponds to the height of the lateral ridges (18, 20).

4. The support plate assembly for teeth according to claim 1, wherein the bottom (32) of the wax receiving surface (22) is equipped with surrounding support flanges (34, 36) which extend below the bottom (32) by a small amount in the range of 0.1 to 1 mm.

5. The support plate assembly for teeth according to claim 4 wherein the surrounding support flanges extend below the bottom (32) about 0.3 mm.

6. The support plate assembly for teeth according to claim 1, wherein the upper ridges (14), lower ridges (16), and lateral ridges (18, 20), each have inner and outer legs (28 and 24), which each extend downward to a common plane for the purpose of creating a flat rest.

7. The support plate assembly for teeth according to claim 1, wherein the upper (14), lower (16) and lateral ridges (18, 20) are hollow.

* * * * *